United States Patent
Miyamoto et al.

(10) Patent No.: US 10,448,640 B2
(45) Date of Patent: Oct. 22, 2019

(54) 2-(3-ETHANESULFONYLPYRIDINE-2-YL)-5-(TRIFLUOROMETHANESULFONYL)BENZOXAZOLE CRYSTAL

(71) Applicant: Sumitomo Chemical Company, Limited, Tokyo (JP)

(72) Inventors: Takashi Miyamoto, Oita (JP); Kosuke Takebayashi, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/062,392

(22) PCT Filed: Dec. 12, 2016

(86) PCT No.: PCT/JP2016/086849
§ 371 (c)(1),
(2) Date: Jun. 14, 2018

(87) PCT Pub. No.: WO2017/104592
PCT Pub. Date: Jun. 22, 2017

(65) Prior Publication Data
US 2018/0368407 A1 Dec. 27, 2018

(30) Foreign Application Priority Data
Dec. 16, 2015 (JP) .................. 2015-244909

(51) Int. Cl.
| | | |
|---|---|---|
| *A01N 43/76* | (2006.01) | |
| *A01N 47/02* | (2006.01) | |
| *C07D 413/04* | (2006.01) | |
| *G01N 23/20* | (2018.01) | |

(52) U.S. Cl.
CPC ............ *A01N 43/76* (2013.01); *A01N 47/02* (2013.01); *C07D 413/04* (2013.01); *G01N 23/20075* (2013.01); *C07B 2200/13* (2013.01)

(58) Field of Classification Search
None
See application file for complete search history.

(56) References Cited

U.S. PATENT DOCUMENTS

2015/0313234 A1 11/2015 Takahashi et al.
2015/0366208 A1 12/2015 Shimizu et al.

FOREIGN PATENT DOCUMENTS

| EP | 2952098 A1 | 12/2015 |
| JP | 201656197 A | 4/2016 |
| WO | 2014104407 A1 | 7/2014 |
| WO | 2014119679 A1 | 8/2014 |
| WO | 2015198817 A1 | 12/2015 |

OTHER PUBLICATIONS

English Translation of International Preliminary Report on Patentability dated Jun. 19, 2018 in International Application No. PCT/JP2016/086849.
English Translation of International Search Report dated Jan. 31, 2017 in International Application No. PCT/JP2016/086849.
Asahara et al., Yozai Handbook, Kodansha Ltd., 6th Print, pp. 47-51 (1985).
Extended European Search Report dated Apr. 24, 2019 in EP16875569.2.
Caira, "Crystalline Polymorphism of Organic Compounds", Topics in Current Chemistry, vol. 198, pp. 163-208, (1998).

*Primary Examiner* — Alton N Pryor
(74) *Attorney, Agent, or Firm* — Panitch Schwarze Belisario & Nadel LLP

(57) ABSTRACT

A type 2 crystal of 2-(3-ethanesulfonylpyridin-2-yl)-5-(trifluoromethanesulfonyl)benzoxazole having diffraction peaks at $2\theta=14.0\pm0.2°$, $14.3\pm0.2°$, $16.5\pm0.2°$, $16.9\pm0.2°$, $17.6\pm0.2°$, $18.8\pm0.2°$, $19.9\pm0.2°$, and $22.3\pm0.2°$ in powder X-ray diffraction using Cu-Kα radiation is a stable crystal.

3 Claims, 3 Drawing Sheets

2-(3-ETHANESULFONYLPYRIDINE-2-YL)-5-(TRIFLUOROMETHANESULFONYL) BENZOXAZOLE CRYSTAL

CROSS-REFERENCE TO RELATED APPLICATION

This application is a Section 371 of International Application No. PCT/JP2016/086849, filed Dec. 12, 2016, which was published in the Japanese language on Jun. 22, 2017, under International Publication No. WO 2017/104592 A1, which claims priority under 35 U.S.C. § 119(b) to Japanese Patent Application No. 2015 244909, filed on Dec. 16, 2015, the disclosures of which are incorporated herein by reference in their entireties.

TECHNICAL FIELD

The present invention relates to a crystal of 2-(3-ethanesulfonylpyridin-2-yl)-5-(trifluoromethanesulfonyl)benzoxazole (hereinafter referred to as "Compound (1)") represented by the following formula (1)

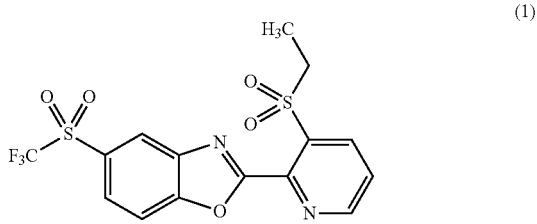 [SMILES: CCS(=O)(=O)c1cccnc1-c1nc2cc(S(=O)(=O)C(F)(F)F)ccc2o1]

(1)

having control efficacies against pests.

BACKGROUND ART

WO 2014/104407 describes that the Compound (1) has control efficacies against pests.

The crystal of the Compound (1) produced in Preparation Example 3 and Preparation Example 17(5) in WO 2014/104407 is a crystal having diffraction peaks at 2θ=13.7±0.2°, 16.2±0.2°, 16.6±0.2°, 17.1±0.2°, 18.8±0.2°, 20.2±0.2°, 21.4±0.2°, and 27.6±0.2° in powder X-ray diffraction using Cu-Kα radiation (hereinafter referred to as "type 1 crystal"), and having diffraction peaks as shown in Table 1.

TABLE 1

| 2θ value (°) | d value (Å) | Relative intensity (%) |
|---|---|---|
| 13.7 | 6.4586 | 25.6 |
| 16.1 | 5.5075 | 22.8 |
| 16.6 | 5.3235 | 35.1 |
| 17.1 | 5.1872 | 22.3 |
| 18.8 | 4.7111 | 16.6 |
| 20.2 | 4.3968 | 56.4 |
| 21.4 | 4.1448 | 100 |
| 27.6 | 3.2338 | 44.6 |

SUMMARY OF THE INVENTION

The present invention provides a more stable crystal of the Compound (1).

The Compound (1) has various crystal forms, and several crystals which are different from one another in the crystal form may be produced by appropriately selecting the solvent used in recrystallization or the temperature in crystallization (for example, Reference Examples 1 to 3). According to the present invention, a crystal having diffraction peaks at 2θ=14.0±0.2°, 14.3±0.2°, 16.5±0.2°, 16.9±0.2°, 17.6±0.2°, 18.8±0.2°, 19.9±0.2°, and 22.3±0.2° (hereinafter referred to as "type 2 crystal") is a stable crystal of the Compound (1).

Using a stable crystal can prevent the decrease in the control efficacies against pests.

A type 2 crystal may be produced by dissolving a type 1 crystal into 2-propanol, followed by precipitating a crystal at the temperature of 65 to 67° C.

Alternatively, a type 2 crystal may also be produced by crystallization from a solvent other than 2-propanol (for example, a mixed solvent of xylene and n-heptane) when a seed crystal of type 2 crystal is present.

DESCRIPTION OF EMBODIMENTS

Figure 1:
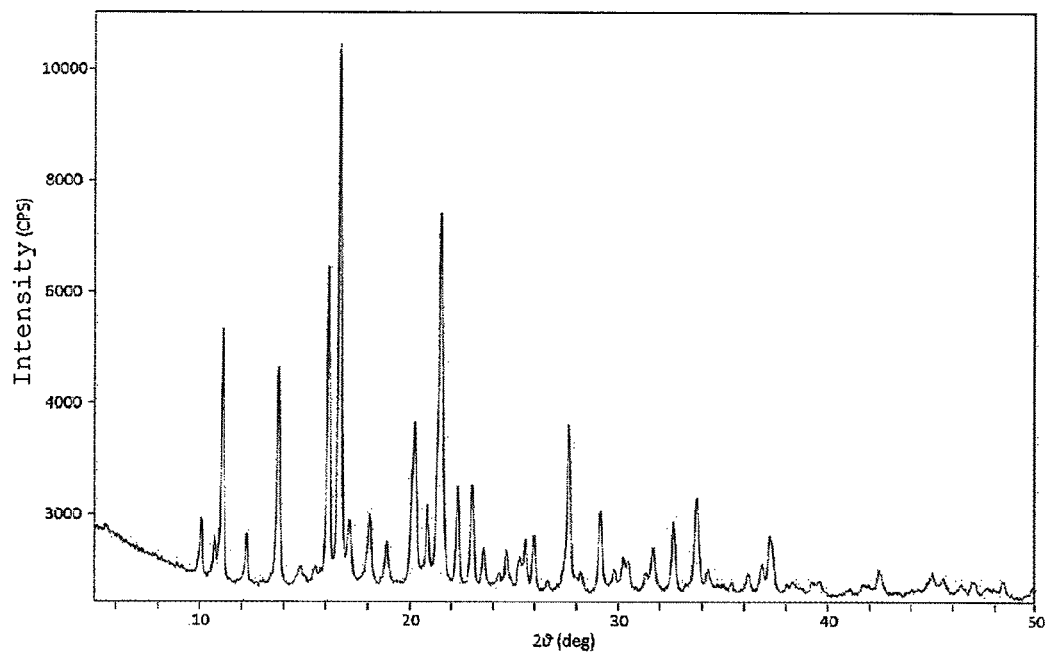
FIG. 1 shows powder X-ray diffraction of a type 1 crystal of the Compound (1).
Figure 2:
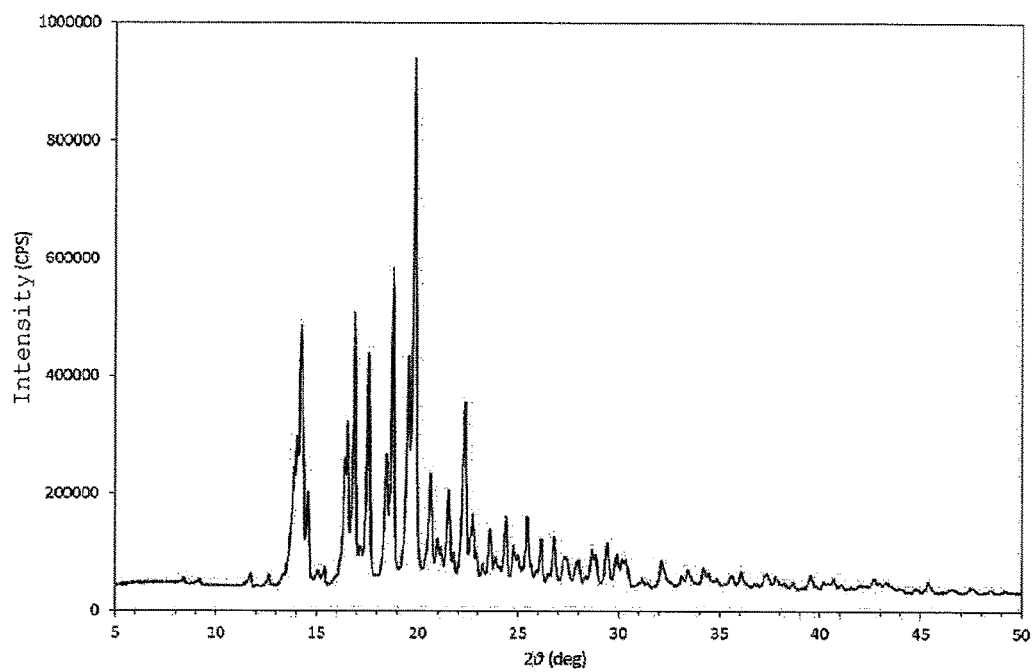
FIG. 2 shows powder X-ray diffraction of a type 2 crystal of the Compound (1).
Figure 3:
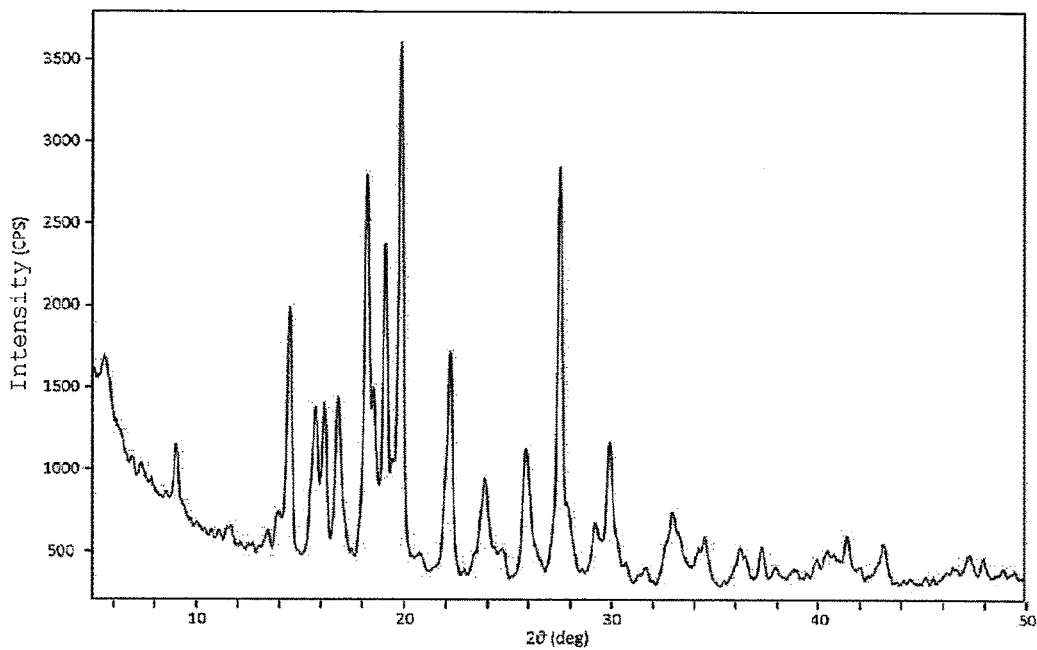
FIG. 3 shows powder X-ray diffraction of a type 3 crystal of the Compound (1).
Figure 4:
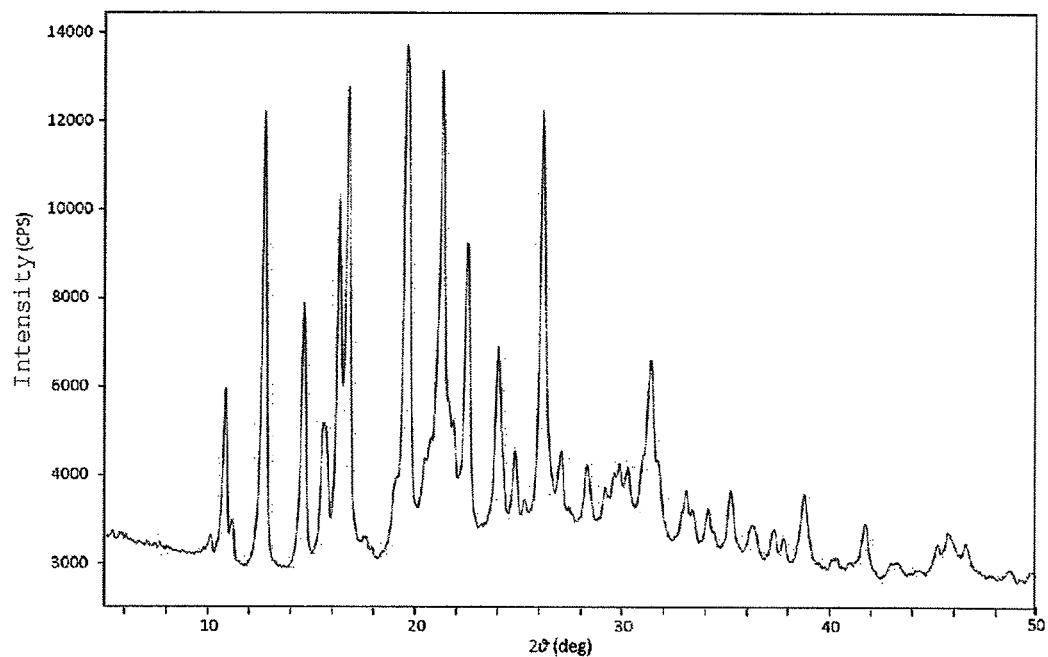
FIG. 4 shows powder X-ray diffraction of a type 4 crystal of the Compound (1).
Figure 5:
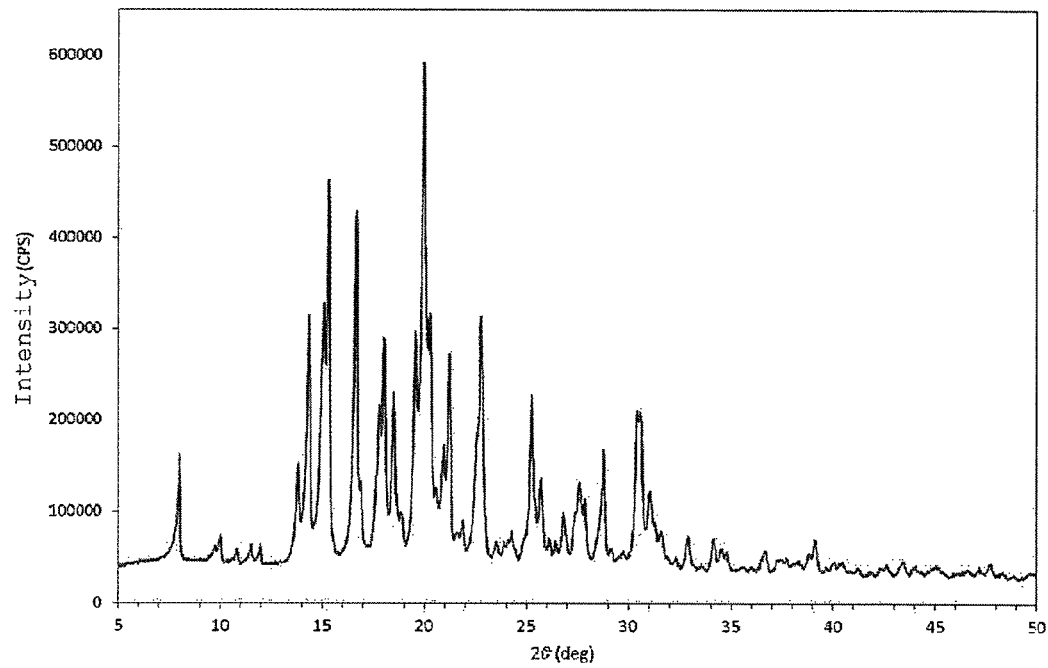
FIG. 5 shows powder X-ray diffraction of a type 5 crystal of the Compound (1).

In the present description, the conditions for the powder X-ray diffraction are as follows.
(Measurement Conditions)
Device for powder X-ray diffraction: SmartLab (manufactured by Rigaku Corporation)
X-ray output: CuKα, 45 kV, 200 mA
Sampling interval: 0.02°
Scan range: 5° to 50°

A type 1 crystal may be produced by concentrating a solution of the Compound (1) in ethyl acetate or chlorobenzene under reduced pressure, followed by drying the resulting residues.

Alternatively, a type 1 crystal may also be produced by adding a poor solvent such as n-heptane to a solution of the Compound (1) in xylene, followed by cooling the resulting mixture.

The present invention relates to a type 2 crystal which is a more stable crystal of the Compound (1). A specific method for producing a type 2 crystal is described below with examples.

1) Type 1 crystals (1 part by weight) are completely dissolved into 2-propanol (6 to 7 parts by weight) at 70° C. to 82° C.

2) The above solution at 70° C. to 82° C. is gradually cooled (for example, at the rate of 3° C./hr) to precipitate crystals at 65° C. to 67° C. If a crystal is not precipitated, a part of 2-propanol may be evaporated to reduce the amount of 2-propanol, and then the solution may be gradually cooled again.

3) The precipitated crystals are filtered and dried to produce type 2 crystals.

A type 2 crystal may also be produced by adding a seed crystal of type 2 crystal to a supersaturated solution of the Compound (1), followed by maintaining the same temperature or gradually cooling the solution (for example, at the rate of 3° C./hr). Examples of the solvent to be used in the crystallization include 2-propanol, a mixed solvent of xylene and n-heptane in a weight ratio of 1:1, and a mixed solvent of xylene and n-heptane in a weight ratio of 7:3. The temperature for precipitating a crystal is 55° C. to 82° C.

Also, the amount of the solvent in precipitating a type 2 crystal is usually within a range of 3 to 20 parts by weight relative to 1 part by weight of the Compound (1).

The amount of the seed crystal used in producing a type 2 crystal is usually 0.001 to 10% by weight, preferably 0.005 to 1% by weight relative to 1 part by weight of the Compound (1).

A pesticide formulation comprising a type 2 crystal (hereinafter referred to as "present pesticide formulation") is more stable than a pesticide formulation comprising a crystal having another crystal form of the Compound (1).

The present pesticide formulation comprises a type 2 crystal and an inert carrier. Examples of the inert carrier include solid carriers and liquid carriers.

Examples of the solid carriers include fine powders or granules of clays (for example, kaolin clay, diatomaceous earth, bentonite, Fubasami clay, pyrophyllite clay, or acid white clay), synthetic hydrated silicon oxide, talc, ceramics, other inorganic minerals (for example, sericite, quartz, sulfur, active carbon, calcium carbonate, or hydrated silica), solids for fertilizer (for example, ammonium sulfate, ammonium phosphate, ammonium nitrate, urea, or ammonium chloride), and the others. Examples of the liquid carriers include water and aliphatic hydrocarbons (for example, kerosene or light oil).

Examples of the pests which may be controlled by the present pesticide formulation include harmful arthropods (for example, harmful insects or harmful acarina), harmful mollusks (for example, harmful Gastropoda), and harmful Nematoda (nematode), and the specific examples thereof include the followings.

Hemiptera pests: *Laodelphax striatellus, Nilaparvata lugens, Sogatella furcifera, Nephotettix cincticeps, Nephotettix virescens, Empoasca onukii, Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Nezara antennata, Eysarcoris parvus, Halyomorpha mista, Riptortus clavetus, Leptocorisa chinensis, Trigonotylus caelestialium, Stenotus rubrovittatus, Trialeurodes vaporariorum, Bemisia tabaci, Dialeurodes citri, Aleurocanthus spiniferus, Aonidiella aurantii, Comstockaspis perniciosa, Unaspis citri, Ceroplastes rubens, Icerya purchasi, Planococcus kraunhiae, Pseudococcus longispinis, Pseudaulacaspis pentagona, Diaphorina citri, Psylla pyrisuga, Bactericerca cockerelli, Stephanitis nasi, Cimex lectularius*, and the others.

Lepidoptera pests: *Chilo suppressalis, Tryporyza incertulas, Cnaphalocrocis medinalis, Notarcha derogata, Plodia interpunctella, Ostrinia furnacalis, Hellula undalis, Pediasia teterrellus, Spodoptera litura, Spodoptera exigua, Pseudaletia separata, Mamestra brassicae, Agrotis Ipsilon, Plusia nigrisigna, Pieris rapae, Grapholita molesta, Leguminivora glycinivorella, Matsumuraeses azukivora, Adoxophyes orana fasciata, Adoxophyes honmai., Homona magnanima, Archips fuscocupreanus, Cydia pomonella, Caloptilia theivora, Phyllonorycter ringoneella, Carposina niponensis, Plutella xylostella, Pectinophora gossypiella, Phthorimaea operculella, Hyphantria cunea*, and the others.

Thysanoptera pests: *Frankliniella occidentalis, Thrips parmi, Scirtothrips dorsalis, Thrips tabaci, Frankliniella intonsa*, and the others.

Diptera pests: *Delia platura, Delia antiqua, Agromyza oryzae, Hydrellia griseola, Liriomyza sativae, Liriomyza trifolii, Chromatomyia horticola, Chlorops oryzae, Dacus cucurbitae, Ceratitis capitata, Megaselia spiracularis, Clogmia albipunctata*, and the others.

Coleoptera pests: *Diabrotica virgifera virgifera, Diabrotica undecimpunctata howardi, Oulema oryzae, Aulacophora femoralis, Phyllotreta striolata, Leptinotarsa decemlineata, Anomala cuprea, Anomala rufocuprea, Popillia japonica, Sitophilus zeamais, Echinocnemus squameus, Lissorhoptrus oryzophilus, Sphenophorus venatus, Anthonomus grandis, Epilachna vigintioctopunctata, Lyctus brunneus, Tomicus piniperda, Anoplophora malasiaca, Agriotes ogurae fuscicollis, Agriotes spp., Paederus fuscipes*, and the others.

Orthoptera pests: *Locusta migratoria, Gryllotalpa africana, Oxya yezoensis, Oxya japonica*, and the others.

Hymenoptera pests: *Athalia rosae, Athalia japonica*, and the others.

Termitidae pests: *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes sp., Nasutitermes takasagoensis, Pericapritermes nitobei, Sinocapritermes mushae*, and the others.

Acarina pests: *Tetranychus urticae, Tetranychus kanzawai, Panonychus citri, Panonychus ulmi, Aculops pelekassi, Phyllocoptruta citri, Aculops lycopersici, Calacarus carinatus, Acaphylla theavagrans, Eriophyes chibaensis, Aculus schlechtendali, Polyphagotarsonemus latus, Brevipalpus phoenicis, Tyrophagus putrescentiae, Tyrophagus similis, Dermatophagoides farinae, Dermatophagoides ptrenyssnus*, and the others.

Chilopoda: *Thereuonema hilgendorfi, Scolopendra subspinipes*, and the others.

Diplopoda: *Oxidus gracilis, Nedyopus tambanus*, and the others.

Isopoda: *Armadillidium vulgare* and the others.

Gastropoda: *Limax marginatus, Limax flavus*, and the others.

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae, Pratylenchus neglectus*, and the others.

Examples of the present pesticide formulation include dosage forms classified as Aqueous suspension concentrates, Wettable powders, Water dispersible granules, or Granules.

Examples of the method for controlling pests using the present pesticide formulation include a method comprising applying an effective amount of the present pesticide formulation to the foliage of plants or the soil where plants are cultivated, and the specific examples thereof include treatment to the foliage of plant such as foliage application, soil treatment, and treatment to plantations of plants such as hydroponic solution treatment. The present pesticide formulation is applied once or two or more times.

Specific examples of the treatment to the foliage of plants include treatment methods comprising applying the present pesticide formulation to surfaces of plants such as foliage application and stem application. Examples of the soil treatment include spraying to soil, soil incorporation, and drenching soil with liquid chemicals. Examples of the place to be treated include planting holes, planting rows, the vicinity of planting holes, the vicinity of planting rows, the entire area of plantation, basal parts of plants, inter-row spaces, places under the stems, ridges between main stems, culture soil, seedling boxes, seedling trays, and seedbeds. Examples of the timing of the treatment include during pre-seeding stages, seeding stages, stages immediately after seeding, and during the growing periods including seedling raising stages, pre-planting stages, planting stages, and post-planting stages. Examples of hydroponic solution treatment include injection into irrigation facilities (an irrigation tube, an irrigation pipe, a sprinkler, and the like), incorporation into a liquid for inter-row space irrigation, and incorporation into a hydroponic solution.

When the present pesticide formulation is used for controlling pests, the application dose of the type 2 crystal is usually 1 to 10,000 g per 10,000 m$^2$. Aqueous suspension concentrates or the like are usually applied by diluting it with water in such a way that a concentration of the type 2 crystal is within a range of 0.01 to 10,000 ppm.

When the present pesticide formulation is applied to paddy rice, the application dose of the type 2 crystal is usually 0.1 to 10 g per a seedling box (inner dimension: 28 cm×58 cm). The type 2 crystal is applied by diluting it with water in such a way that the concentration thereof is within a range of 0.01 to 10,000 ppm, or the present pesticide formulation is directly applied to a seedling box.

The present pesticide formulation may be used in farm land where various plants are cultivated. For example, the present pesticide formulation or its dilution with water may be used in farm land where the following plants are cultivated.

Crops: corn, rice, wheat, barley, rye, oat, sorghum, cotton, soybean, peanut, buckwheat, beet, rapeseed, sunflower, sugar cane, tobacco, and the others;

Vegetables: solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, carrot, parsley, celery, or parsnip), chenopodiaceous vegetables (for example, spinach or Swiss chard), lamiaceous vegetables (for example, perilla, mint, or basil), strawberry, sweet potato, glutinous yam, eddoe, and the others;

Fruits: pomaceous fruits (for example, apple, pear, Japanese pear, Chinese quince, or quince), stone fleshy fruits (for example, peach, plum, nectarine, Japanese apricot (*Prunus mume*), cherry fruit, apricot, or prune), citrus fruits (for example, *Citrus unshiu*, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, oil palm, and the others;

Trees other than fruit trees: tea, mulberry, flowering plants (for example, Satuki azalea (*Rhododendron indicum*), camellia, hydrangea, sasanqua, skimmia, cherry, tulip tree, crape myrtle, or orange osmanthus), roadside trees (for example, ash, birch, dogwood, *eucalyptus*, ginkgo (*ginkgo biloba*), lilac, maple, oak (*quercus*), poplar, Judas tree, Formosan gum (*Liquidambar formosana*), plane tree, *zelkova*, Japanese arborvitae (*Thuja standishii*), fir wood, hemlock, juniper, *pinus, picea*, yew (*Taxus cuspidate*), elm, or buckeye), sweet *viburnum*, shrubby Japanese yew (*Podocarpus macrophyllus*), Japanese cedar, hinoki cypress, croton, Japanese spindle tree (*Euonymus japonicus*), Japanese *photinia* (*Photinia glabra*), and the others;

Turfgrass: *Zoysia* (for example, zoysiagrass (*Zoysia japonica*) or Korean lawn grass (*Zoysia tenuifolia*)), *Cynodon* (for example, bermuda grass), *Agrostis* (bentgrasses) (for example, creeping bentgrass (*Agrostis alba*), *Agrostis stolonifera*, or *Agrostis capillaris*), Poa (blueglasses) (for example, Kentucky bluegrass or rough bluegrass), *Festuca* (for example, tall fescue (*Festuca arundinacea*), chewing fescue (*Festuca rubra* var. *commutata*), or creeping red fescue (*Festuca rubra* var.)), *Lolium* (ryegrasses) (for example, Italian ryegrass or perennial ryegrass), orchard grass, timothy, and the others;

Other plants: Flowers (for example, rose, carnation, *chrysanthemum*, showy prairie gentian, annual baby's breath, *gerbera*, marigold, *salvia, petunia, verbena*, tulip, aster, gentian, lily, pansy, cyclamen, orchid, lily of the valley, lavender, stock, ornamental cabbage, *primula*, poinsettia, *gladiolus*, cattleya, daisy, cymbidium, or *begonia*), biofuel plants (for example, Jatropha, curcas, safflower, Camelina, switchgrass, *miscanthus*, reed canary grass, giant reed, kenaf, cassava, willow, or algae), foliage plants, and the others.

The above plants also include genetically engineered plants.

The present pesticide formulation may be mixed with or used in combination with other insecticides, acaricides, nematicides, fungicides, herbicides, synergists, safeners, or plant growth regulators. For example, the present pesticide formulation may be mixed with or used in combination with the active ingredients of the following insecticides, acaricides, nematicides, fungicides, herbicides, synergists, safeners, or plant growth regulators.

Active ingredients of insecticides, acaricides, or nematicides (1) Organophosphorus Compounds acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos (CYAP), demeton-S-methyl, diazinon, dichlorvos (DDVP), dicrotophos, dimethoate, dimethylvinphos, disulfoton, EPN, ethion, ethoprophos, famphur, fenamiphos, fenitrothion (MEP), fenthion (MPP), heptenophos, isofenphos, isopropyl-O-(methoxyaminothiophosphoryl)salicylate or isocarbophos, isoxathion, malathion, mecarbam, methamidophos, methidathion (DMTP), mevinphos, monocrotophos, naled (BRP), omethoate, oxydemeton-methyl, parathion, parathion-methyl or methyl parathion, phenthoate (PAP), phorate, phosalone, phosmet (PMP), phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon (DEP), and vamidothion;

(2) Carbamate Compounds alanycarb, aldicarb, bendiocarb, benfuracarb, butocarboxim, butoxycarboxim, carbaryl (NAC), carbofuran, carbosulfan, ethiofencarb, fenobucarb (BPMC), formetanate, furathiocarb, isoprocarb (MIPC), methiocarb, methomyl, metolcarb, oxamyl, pirimicarb, propoxur (PHC), thiodicarb, thiofanox, triazamate, trimethacarb, XMC, and xylylcarb;

(3) Synthetic Pyrethroid Compounds acrinathrin, allethrin, bifenthrin, bioallethrin, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, fluvalinate, tau-fluvalinate, halfenprox, heptafluthrin, imiprothrin, kadethrin, meperfluthrin, momfluorothrin, permethrin, phenothrin, prallethrin, pyrethrins, resmethrin, silafluofen, tefluthrin, tetramethrin, tetramethylfluthrin, tralomethrin, and transfluthrin;

(4) Nereistoxin Compounds bensultap, cartap, cartap hydrochloride, thiocyclam, thiosultap-disodium or bisultap, and thiosultap-monosodium or monosultap;

(5) Neonicotinoid Compounds acetamiprid, clothianidin, dinotefuran, flupyradifurone, imidacloprid, nitenpyram, sulfoxaflor, thiacloprid, and thiamethoxam;

(6) Benzoylurea Compounds bistrifluron, chlorfluazuron, diflubenzuron, flucycloxuron, flufenoxuron, hexaflumuron, lufenuron, novaluron, noviflumuron, teflubenzuron, and triflumuron;

(7) Phenylpyrazole Compounds ethiprole, fipronil, and flufiprole;

(8) Hydrazine Compounds chromafenozide, halofenozide, methoxyfenozide, and tebufenozide;

(9) Organochlorine Compounds chlordane, endosulfan, and alpha-endosulfan;

(10) Diamide Compounds chlorantraniliprole, cyantraniliprole, cycloniliprole, flubendiamide, and tetraniliprole;

(11) Natural Insecticides machine oil, nicotine-sulfate, and rotenone;

(12) Microbial Materials raw spores derived from *Bacillus thuringiensis*, var. *aizawai*, var. *kurstaki*, var. *israelensis*, or var. *tenebriosis*, produced crystal toxins thereof, and mixtures thereof, *Bacillus sphaericus*, *Beauveria bassiana* (for example, strain GHA), *Beauveria brongniartii*, *Paecilomyces fumosoroseus*, *Paecilomyces lilacinus*, *Paecilomyces tenuipes*, *Trichoderma harzianum*, and *Verticillium lecani*;

(13) Nematicidal Active Compounds dazomet, fluensulfone, fosthiazate, imicyafos, metam, potassium antimonyl tartrate trihydrate, tioxazafen, *Arthrobotrys dactyloides*, *Bacilus firmus* (for example, strain 1-1582), *Bacillus megaterium*, *Hirsutella rhossiliensis*, *Hirsutella minnesotensis*, *Monacrosporium phymatopagus*, *Pasteuria nishizawae*, *Pasteuria penetrans*, *Pasteuria usgae*, *Verticillium chlamydosporium*, and Harpin protein;

(14) Other Acaricidal Active Compounds acequinocyl, amitraz, benzoximate, bifenazate, bromopropylate, chinomethionat, clofentezine, cyenopyrafen, cyflumetofen, cyhexatin or tricyclohexyltin hydroxide, dicofol, etoxazole, fenazaquin, fenbutatin oxide, fenpyroximate, fluacrypyrim, fluazuron, flufenoxystrobin, hexythiazox, propargite (BPPS), pyflubumide, pyridaben, pyrimidifen, pyriminostrobin, spirodiclofen, spiromesifen, tebufenpyrad, and tetradifon;

(15) Other Insecticides abamectin, emamectin-benzoate, lepimectin, milbemectin, spinetoram, spinosad, afidopyropen, aluminium phosphide, calcium phosphide, phosphine, zinc phosphide, azadirachtin, buprofezin, chlorfenapyr, chloropicrin, cyromazine, diafenthiuron, DNOC, fenoxycarb, flometoquin, flonicamid, hydramethylnon, hydroprene, indoxacarb, kinoprene, metaflumizone, methoprene, methoxychlor, methyl bromide, metoxadiazone, pymetrozine, pyrazophos, pyridalyl, pyrifluquinazone, pyriproxyfen, sodium aluminium fluoride or chiolite, spirotetramat, sulfluramid, sulfuryl fluoride, tolfenpyrad, and triflumezopyrim.

Active Ingredients of Fungicides (1) DMI Fungicides (Demethylation Inhibitors)

azaconazole, bitertanol, bromuconazole, cyproconazole, difenoconazole, diniconazole, diniconazole-M, epoxyconazole, etaconazole, fenarimol, fenbuconazole, fluquinconazole, flusilazole, flutriafol, hexaconazole, imazalil, imibenconazole, ipconazole, metconazole, myclobutanil, nuarimol, oxpoconazole, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, and triticonazole;

(2) Amine Fungicides aldimorph, dodemorph, fenpropidin, fenpropimorph, piperalin, spiroxamine, and tridemorph;

(3) Benzimidazole Fungicides benomyl, carbendazim, fuberidazole, thiabendazole, thiophanate, and thiophanate-methyl;

(4) Dicarboximide Fungicides chlozolinate, iprodione, procymidone, and vinclozolin;

(5) Anilinopyrimidine Fungicides cyprodinil, mepanipyrim, and pyrimethanil;

(6) Phenylpyrrole Fungicides fenpiclonil and fludioxonil;

(7) QoI Inhibitors azoxystrobin, coumoxystrobin, dimoxystrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb, triclopyricarb, trifloxystrobin, and N-methyl-2-[2-(2,5-dimethylphenoxy)methyl]phenyl-2-methoxyacetamide (including a racemate or an enantiomer, and a mixture of an arbitrary ratio of R-enantiomer and S-enantiomer);

(8) PA Fungicides (Phenyl Amide Fungicides)

benalaxyl, benalaxyl-M or kiralaxyl, furalaxyl, metalaxyl, metalaxyl-M or mefenoxam, oxadixyl, and ofurace;

(9) Carboxylic Acid Amide Fungicides dimethomorph, flumorph, pyrimorph, benthiavalicarb, benthivalicarb-isopropyl, iprovalicarb, mandipropamid, and valifenalate;

(10) SDHI Fungicides benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penthiopyrad, penflufen, sedaxane, thifluzamide, and a compound represented by the following formula (a);

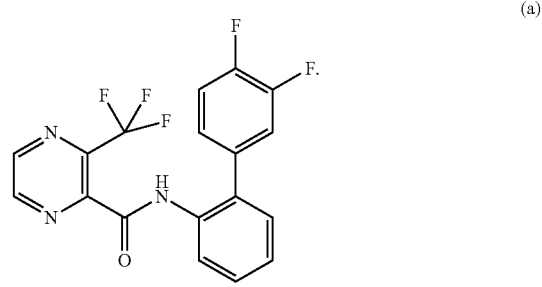 [SMILES: O=C(Nc1ccccc1-c1ccc(F)c(F)c1)c1nccnc1C(F)(F)F]

(a)

(11) Dithiocarbamate Fungicides
ferbam, mancozeb or manzeb, maneb, metiram, propineb, thiram, zineb, and ziram;
(12) MBI-R agents
phthalide or fthalide, pyroquilone, and tricyclazole;
(13) MBI-D agents
carpropamide, diclocymet, and fenoxanil;
(14) Microbial Materials
*Agrobacterium radiobactor* (for example, strain 84), *Bacillus amyloliquefaciens*, *Bacillus pumulus*, *Bacillus simplex* (for example, strain CGF2856), *Bacillus subtilis* (synonyms for *Bacillus amyloliquefaciens*) (for example, strain QST713, strain FZB24, strain MBI600, strain D747, strain HAI0404, or strain Y1336), *Variovorax paradoxus* (for example, strain CGF4526), *Erwinia carotovora* (for example, strain CGE234M403), *Pseudomonas fluorescens* (for example, strain G7090), *Talaromyces flavus* (for example, strain SAY-Y-94-01), and *Trichoderma atroviride* (for example, strain SKT-1);
(15) Other Fungicides
acibenzolar-S-methyl, ametoctradin, amisulbrom, anilazine, biphenyl, blasticidin-S, bupirimate, captafol, captan, chinomethionat or quinomethionate, chloroneb, chlorothalonil, cyazofamid, cyflufenamid, cymoxanil, dichlofluanid, diclomezine, dicloran, diethofencarb, diflumetorim, dimethirimol, dinocap, dithianon, dodine, echlomezol or etridiazole, edifenphos, ethaboxam, ethirimol, fenhexamid, fenpyrazamine, fentin acetate, fentin chloride, fentin hydroxide, ferimzone, fluazinam, fluopicolide, fluoroimide, flusulfamide, flutianil, folpet, fosetyl, guazatine, hymexazol, iminoctadine, iminoctadine triacetate, iodocarb, iprobenfos, isoprothiolane, isotianil, kasugamycin, laminarin, meptyldinocap, methasulfocarb, metrafenone, octhilinone, oxathiapiprolin, oxolinic acid, oxytetracycline, pencycuron, polyoxins, probenazole, propamocarb, proquinazid, prothiocarb, pyrazophos, pyributicarb, pyriofenone, quinoxyfen, quintozene, streptomycin, tebufloquin, tecloftalam, tecnazene, tiadinil, tolclofos-methyl, tolfenpyrad, tolylfluanid, tolprocarb, triazoxide, validamycin A, zoxamide, basic copper chloride, copper(II) hydroxide, basic copper sulfate, organic copper, sulfur, 3-chloro-5-phenyl-6-methyl-4-(2,6-difluorophenyl)pyridazine, 3-cyano-5-phenyl-6-methyl-4-(2,6-difluorophenyl)pyridazine, N-(1,1,3-trimethylindan-4-yl)-1-methyl-3-difluoromethylpyrazole-4-carboxylic acid amide (including a racemate or an enantiomer, and a mixture of an arbitrary ratio of R-enantiomer and S-enantiomer); a compound represented by the following formula (b);

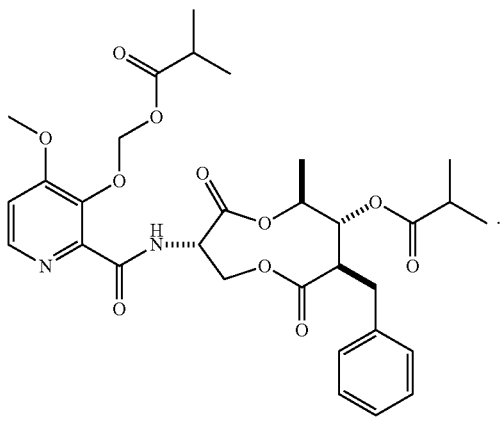

a compound represented by the following formula (c);

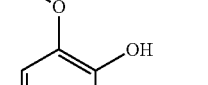

and a compound represented by the following formula (d);

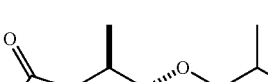

Active Ingredients of Herbicides
(1) Phenoxy Fatty Acid Herbicidal Compounds:
2,4-PA, MCP, MCPB, phenothiol, mecoprop, fluroxypyr, triclopyr, clomeprop, and naproanilide.
(2) Benzoic Acid Herbicidal Compounds:
2,3,6-TBA, dicamba, clopyralid, picloram, aminopyralid, quinclorac, and quinmerac.
(3) Urea Herbicidal Compounds:
diuron, linuron, chlortoluron, isoproturon, fluometuron, isouron, tebuthiuron, methabenzthiazuron, cumyluron, daimuron, and methyl-daimuron.
(4) Triazine Herbicidal Compounds:
atrazine, ametoryn, cyanazine, simazine, propazine, simetryn, dimethametryn, prometryn, metribuzin, triaziflam, and indaziflam.
(5) Bipyridinium Herbicidal Compounds:
paraquat and diquat.
(6) Hydroxybenzonitrile Herbicidal Compounds:
bromoxynil and ioxynil.
(7) Dinitroaniline Herbicidal Compounds:
Pendimethalin, Prodiamine, and Trifluralin.
(8) Organophosphorus Herbicidal Compounds:
amiprofos-methyl, butamifos, bensulide, piperophos, anilofos, glyphosate, glufosinate, glufosinate-P, and bialaphos.
(9) Carbamate Herbicidal Compounds:
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds:
propanil, propyzamide, bromobutide, and etobenzanid.
(11) Chloroacetanilide Herbicidal Compounds:
acetochlor, alachlor, butachlor, dimethenamid, propachlor, metazachlor, metolachlor, pretilachlor, thenylchlor, and pethoxamid.

(12) Diphenylether Herbicidal Compounds:
    acifluorfen-sodium, bifenox, oxyfluorfen, lactofen, fomesafen, chlomethoxynil, and aclonifen.
(13) Cyclic Imide Herbicidal Compounds:
    oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds:
    benzofenap, pyrazolate, pyrazoxyfen, topramezone, and pyrasulfotole.
(15) Triketone Herbicidal Compounds:
    isoxaflutole, benzobicyclon, sulcotrione, mesotrione, tembotrione, and tefuryltrione.
(16) Aryloxy Phenoxypropionic Acid Herbicidal Compounds:
    clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds:
    alloxydim-sodium, sethoxydim, butroxydim, clethodim, cloproxydim, cycloxydim, tepraloxydim, tralkoxydim, and profoxydim.
(18) Sulfonylurea herbicidal compounds:
    chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds:
    imazamethabenz-methyl, imazamethapyr, imazamox, imazapyr, imazaquin, and imazethapyr.
(20) Sulfonamide Herbicidal Compounds:
    flumetsulam, metosulam, diclosulam, florasulam, cloransulam-methyl, penoxsulam, and pyroxsulam.
(21) Pyrimidinyl Oxybenzoic Acid Herbicidal Compounds:
    pyrithiobac-sodium, bispyribac-sodium, pyriminobac-methyl, pyribenzoxim, pyriftalid, and pyrimisulfan.
(22) Other Herbicidal Compounds:
    bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.
Active Ingredients of Synergists
    piperonyl butoxide, sesamex, sulfoxide, N-(2-ethylhexyl)-8,9,10-trinorborn-5-ene-2,3-dicarboximide (MGK264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.
Active Ingredients of Safeners
    benoxacor, cloquintocet, cloquintocet-mexyl, cyometrinil, cyprosulfamide, dichlormid, dicyclonon, diethotate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride, and oxabetrinil.
Active Ingredients of Plant Growth Regulators
    chlormequat-chloride, ethephon, gibberellins (for example, Gibberellin A3), hymexazol, inabenfide, mepiquat-chloride, 1-methylcyclopropene, paclobutrazol, prohexadione, prohexadione-calcium, trinexapac, trinexapac-ethyl, uniconazole, uniconazole-P, 4-oxo-4-(2-phenylethyl) aminobutyric acid, and methyl 5-(trifluoromethyl)benzo[b]thiophene-2-carboxylate.

EXAMPLES

The following Examples serve to illustrate the present invention more in detail, which should not intend to limit the present invention.

Example 1

2-propanol (6.3 parts by weight) was added to a separable flask, and warmed to 73° C. Type 1 crystals (1 part by weight) were added to the separable flask at 73° C., and the resulting mixture was stirred to completely dissolve the crystals. The temperature of the resulting solution was lowered at the rate of 3° C./hr under stirring, and then crystals began to precipitate at 67° C., and the temperature was further lowered to room temperature, and the solids were collected from the resulting mixture by filtration to give type 2 crystals.

The resulting type 2 crystals showed the diffraction peaks in powder X-ray diffraction using Cu-Kα radiation as shown in Table 2.

TABLE 2

| 2θ value (°) | d value (Å) | Relative intensity (%) |
|---|---|---|
| 14.0 | 6.3197 | 51.4 |
| 14.3 | 6.2057 | 100 |
| 16.5 | 5.368 | 25.1 |
| 16.9 | 5.2423 | 38.5 |
| 17.6 | 5.0404 | 21.2 |
| 18.8 | 4.721 | 39 |
| 19.9 | 4.4667 | 82.7 |
| 22.3 | 3.9796 | 22.3 |

Example 2

A mixture of xylene (16.0 parts by weight) and n-heptane (16.0 parts by weight) was added to a separable flask, and warmed to 75° C. Type 1 crystals (1 part by weight) were added to the separable flask at 75° C., and the resulting mixture was stirred to completely dissolve the crystals. The temperature of the resulting mixture was lowered at the rate of 5° C./hr under stirring, and a seed crystal of type 2 crystal was added thereto when the temperature of the solution was 55° C. Then, crystals began to precipitate from the solution, and the temperature of the mixture was lowered at the rate of 5° C./hr under stirring to room temperature. The solids were collected from the resulting mixture by filtration to give the type 2 crystals.

For reference, preparation examples of crystals of the Compound (1) which are different from the type 1 crystal and the type 2 crystal are described as Reference Examples. These crystals are all less stable than the type 2 crystal.

Reference Example 1

To type 1 crystals (1 part by weight) was added methanol (25 parts by weight) at room temperature to dissolve the crystals. The resulting solution was left to stand at room temperature for about 1 day to allow methanol to gradually evaporate, and the resulting solids were filtered to give crystals (hereinafter referred to as "type 3 crystals").

The resulting type 3 crystals showed the diffraction peaks in powder X-ray diffraction using Cu-Kα radiation as shown in Table 3.

TABLE 3

| 2θ value (°) | d value (Å) | Relative intensity (%) |
| --- | --- | --- |
| 14.5 | 6.0952 | 45.3 |
| 15.8 | 5.6117 | 33.6 |
| 16.2 | 5.4735 | 27.6 |
| 16.8 | 5.2603 | 26.6 |
| 18.2 | 4.8597 | 67.5 |
| 19.1 | 4.6381 | 37.8 |
| 19.9 | 4.4668 | 100 |
| 22.2 | 3.9974 | 45.7 |
| 23.9 | 3.7261 | 27.8 |
| 25.9 | 3.4372 | 33.9 |
| 27.5 | 3.2361 | 80.2 |
| 29.9 | 2.9839 | 43.6 |

Reference Example 2

To type 1 crystals (1 part by weight) was added methyl t-butyl ether (60 parts by weight) at room temperature to dissolve the crystals. The resulting solution was left to stand at room temperature for about 1 day to allow methyl t-butyl ether to gradually evaporate, and the resulting solids were filtered to give crystals (hereinafter referred to as "type 4 crystals").

The resulting type 4 crystals showed diffraction peaks in powder X-ray diffraction using Cu-Kα radiation as shown in Table 4.

TABLE 4

| 2θ value (°) | d value (Å) | Relative intensity (%) |
| --- | --- | --- |
| 10.9 | 8.1257 | 24.4 |
| 12.8 | 6.9316 | 60.5 |
| 14.7 | 6.0371 | 33.1 |
| 16.4 | 5.4137 | 64.9 |
| 16.8 | 5.2671 | 63.3 |
| 19.7 | 4.4984 | 100 |
| 21.4 | 4.1527 | 99.2 |
| 22.6 | 3.9379 | 35.5 |
| 24.0 | 3.6989 | 24.3 |
| 26.2 | 3.3961 | 45.2 |
| 31.4 | 2.85 | 33.9 |

Reference Example 3

To xylene (5.0 parts by weight) was added type 1 crystals (1 part by weight) at 65° C. to dissolve the crystals. The resulting solution was added dropwise to n-heptane (5.0 parts by weight) at 25° C. to precipitate solids. After the whole amount of the solution was added dropwise, the resulting mixture was cooled to room temperature under stirring, and the precipitated solids were filtered to give crystals (hereinafter referred to as "type 5 crystals").

The resulting type 5 crystals showed the diffraction peaks in powder X-ray diffraction using Cu-Kα radiation as shown in Table 5.

TABLE 5

| 2θ value (°) | d value (Å) | Relative intensity (%) |
| --- | --- | --- |
| 8.0 | 11.0092 | 28.8 |
| 13.8 | 6.4018 | 26.0 |
| 14.4 | 6.1623 | 82.2 |
| 14.9 | 5.9219 | 29.7 |
| 15.1 | 5.8709 | 63.0 |
| 16.7 | 5.3167 | 77.9 |
| 17.8 | 4.9781 | 59.2 |
| 18.0 | 4.9203 | 30.3 |
| 18.5 | 4.7950 | 29.8 |
| 19.5 | 4.5381 | 63.3 |
| 20.0 | 4.4399 | 100.0 |
| 22.7 | 3.9148 | 56.2 |
| 25.2 | 3.5255 | 56.5 |
| 30.6 | 2.9203 | 40.4 |

Next, Formulation examples of the present pesticide formulation are shown below.

Formulation Example 1

Type 2 crystals (20 parts by weight), sodium lauryl sulfate (4 parts by weight), calcium lignin sulfonate (2 parts by weight), silica fine powder (20 parts by weight), and diatomaceous earth (54 parts by weight) are mixed to obtain a 20% wettable powder.

Formulation Example 2

Type 2 crystals (2 parts by weight), silica fine powder (1 part by weight), calcium lignin sulfonate (2 parts by weight), bentonite (30 parts by weight), and kaolin (65 parts by weight) are mixed. To the resulting mixture is added an appropriate amount of water, and the resulting mixture is kneaded. The resulting kneaded product is subjected to extruding granulation with a granulator and forced-air drying to obtain a 2% granule.

Formulation Example 3

Type 2 crystals (2 parts by weight), a binder (5 parts by weight), a non-ionic surfactant (1 part by weight), and pyrophyllite clay (92 parts by weight) were mixed. To the resulting mixture was added an appropriate amount of water, and the resulting mixture was kneaded. The resulting kneaded product was subjected to extruding granulation with a basket type granulator and forced-air drying to obtain a 2% granule having φ1.2 mm.

Formulation Example 4

A mixture of polyoxyethylene alkyl ether sulfate ammonium salt and white carbon (weight ratio of 1:1) (35 parts by weight), type 2 crystals (10 parts by weight), and water (55 parts by weight) are fully mixed to obtain a 10% flowable formulation.

Next, the control efficacies against pests of the present pesticide formulation are shown below.

Test Example 1

The 2% granule comprising the type 2 crystals obtained in the Formulation example 3 (hereinafter referred to as "present granule 1") and a 2% granule obtained according to the Formulation example 3 by using type 1 crystals instead of the type 2 crystals (hereinafter referred to as "comparative granule 1") were prepared.

To the plant foot soil of one stock of rice seedling (*Oryza sativa*, cultivar: Hinohikari) with 2.5 leaf stage planted in a cell tray with 200 holes was applied the present granule 1 or the comparative granule 1 (50 mg), and then ion exchanged water (0.5 ml) was added dropwise thereto. After being left to stand in a room for 1.5 hours, the rice seedling and the soil in the cell tray were transplanted into a Wagner pot (area: 1/5000a) containing flooded soil, and grown in a greenhouse (25° C.). After 50 days from the transplantation, the whole rice was covered with a nylon gauze, and brown planthoppers (*Nilaparvata lugens*) (6 heads of female 5th instar larvae just before eclosion and 3 heads of male adults just before eclosion per one pot) were released thereto. After 24 days from the release of the brown planthoppers, the number of the eclosed larvae lived on the rice was investigated (hereinafter referred to as "test group").

A rice seedling was grown in a similar manner to the test group except that treatment with the granule comprising the Compound (1) was not made. After 50 days from the transplantation, brown planthoppers were released to the rice like the test group, and the number of the eclosed larvae lived on the rice was investigated (hereinafter referred to as "control group").

Control effect was calculated according to the following equation on the basis of the observations in the test group and the control group (each test was carried out 3 iterations, and the average value was calculated).

Control effect (%)=100−(number of insects in test group/number of insects in control group)×100

TABLE 6

| Granule | Control effect (%) |
| --- | --- |
| Present granule 1 | 100 |
| Comparative granule 1 | 85 |

INDUSTRIAL APPLICABILITY

The type 2 crystal is a stable crystal of 2-(3-ethanesulfonylpyridin-2-yl)-5-(trifluoromethanesulfonyl)benzoxazole, and may be used for controlling pests.

The invention claimed is:

1. A type 2 crystal of 2-(3-ethanesulfonylpyridin-2-yl)-5-(trifluoromethanesulfonyl)benzoxazole, wherein the crystal has diffraction peaks at $2\theta$=14.0±0.2°, 14.3±0.2°, 16.5±0.2°, 16.9±0.2°, 17.6±0.2°, 18.8±0.2°, 19.9±0.2°, and 22.3±0.2° in powder X-ray diffraction using Cu-K$\alpha$ radiation.

2. A pesticide formulation comprising the type 2 crystal according to claim 1 as an active ingredient.

3. A method for producing the type 2 crystal according to claim 1 wherein the method comprises dissolving a type 1 crystal of 2-(3-ethanesulfonylpyridin-2-yl)-5-(trifluoromethanesulfonyl)benzoxazole having diffraction peaks at $2\theta$=13.7±0.2°, 16.2±0.2°, 16.6±0.2°, 17.1±0.2°, 18.8±0.2°, 20.2±0.2°, 21.4±0.2°, and 27.6±0.2° in powder X-ray diffraction using Cu-K$\alpha$ radiation into 2-propanol, and precipitating the type 2 crystal at a temperature of 65 to 67° C.

* * * * *